US006214615B1

(12) United States Patent
Brann et al.

(10) Patent No.: US 6,214,615 B1
(45) Date of Patent: Apr. 10, 2001

(54) CLONED GENES FOR HUMAN DOPAMINE D2 RECEPTORS AND CELL LINES EXPRESSING SAME

(75) Inventors: Mark R. Brann; Thomas M. Stormann, both of Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 08/709,298

(22) Filed: Sep. 9, 1996

Related U.S. Application Data

(62) Division of application No. 07/413,026, filed on Sep. 27, 1989, now Pat. No. 5,554,500.

(51) Int. Cl.$^7$ ............................. C12N 5/10; C12N 15/63; C07H 21/04
(52) U.S. Cl. .................. 435/361; 435/69.1; 435/320.1; 435/325; 536/23.5
(58) Field of Search ................ 435/69.1, 172.1, 435/320.1, 325, 361; 536/23.5

(56) References Cited

PUBLICATIONS

Stormann et al., "Molecular Cloning and Expression of a Dopamine D2 Receptor from Human Retina", *Molecular Pharmacology*, 37:1–6.
Grandy et al., "Cloning of the cDNA and Gene for a Human D2 Dopamine Receptor", *Proc. Nat'l Acad. Sci.*, vol. 86, Dec., 1989, pp. 9672–9766.
Toso et al., "Dopamine D2 Receptor: Two Molecular Forms Generated By Alternative Splicing", *EMBO Journal*, vol. 8, No. 13, pp. 4025–4034, 1989.
Botsein et al., "Strategies and Application of in Vitro Mutagenesis", *Science*, vol. 228, No. 4719, Sep. 1985, pp. 1193–1201.
Sokoloff et al., "Molecular Cloning and Characterization of a Novel Dopamine Receptor (D3) as a Target for Neuroleptics", *Nature*, vol. 347, Sep., 1990, pp. 146–151.
Tol et al., "Cloning of the Gene for a Human Dopamine D4 Receptor With High Affinity for the Antipsychotic Clozapine", *Letters to Nature*, vol. 350, Apr., 1991, pp. 610–614.
Tiberi et al., Cloning Molecular Characterization and Chromosomal Assignment of a Gene Encoding a Second D1 Dopamine Receptor Subtype: Differential Expression Pattern in Rat Brain Compared With the D1A Receptor, *Proc. Natl. Sci. USA*, vol. 88, Sep. 1991, pp. 7491–7495.
Sunahara et al., "Cloning of the Gene for a Human Dopamine D5 Receptor With Higher Affinity for Dopamine than D1", *Letters to Nature*, vol. 350, Apr. 1991, pp. 614–619.
Brunzow et al., Cloning and Express of a Rat $D_2$ Dopamine Receptor cDNA, *Nature*, vol. 336, 22/29, Dec. 1988.
Kobilka et al., "cDNA for the human $\beta_2$-adrenergic receptor: A protein with multiple membrane–spanning domains and encoded by a gene whose chromosomal location is shared with that of the receptor for platelet–derived growth factor", *Proc. Natl. Acad. Sci.*, vol. 84, pp. 46–50, Jan. 1987, pp. 46–50.
McGonigle et al., "A Comprehensive Method for the Quantitative Determination of Dopamine Receptor Subtypes", *Annals of the New York Academy of Sciences*, vol. 430, Jul. 5, 1984, pp. 77–90.
Reeck et al., *Cell*, vol. 50, p. 667, 1987.*
Emorine et al., *PNAS*, vol. 84, pp. 6995–6999, 1987.*
Wouters et al., *Biochem. Pharmac.*, vol. 33, pp. 4039–4044, 1984.*

* cited by examiner

Primary Examiner—Gary L. Kunz
Assistant Examiner—Stephen Gucker
(74) *Attorney, Agent, or Firm*—Fitch, Even, Tabin & Flannery

(57) ABSTRACT

Disclosed herein is an isolated or essentially pure DNA sequence encoding a human Dopamine D2 receptor, the protein comprising the receptor, vectors for transforming or transfecting host cells with such DNA so that the cells express the DNA, methods of obtaining the DNA and preparing the transformed or transfected cells and cell lines, and methods of using the cells and cell lines in assays for the determination of human dopamine D2 receptor antagonists or agonists.

11 Claims, 7 Drawing Sheets

Fig. 2A

```
     -168 GAATTCCGGCCTCCCGGCCGAGGAGAGTGGCGG
CCCCGGACGGCTGCCGGAGGGGCGGCCGCGCGTGGATGCGGCGGG
AGCTGGAAGCCTCAAGCAGCCGGCGCCGTCTCTGCCCCGGGGCGC
CCTATGGCTTGAAGAGCCTGGCCACCCAGTGGCTCCACCGCCCTG
                         10
MetAspProLeuAsnLeuSerTrpTyrAspAspAspLeuGluArg
ATGGATCCACTGAATCTGTCCTGGTATGATGATGATCTGGAGAGG
0
             20                   Glu       30
GlnAsnTrpSerArgProPheAsnGlySerAspGlyLysAlaAsp
CAGAACTGGAGCCGGCCCTTCAACGGGTCAGACGGGAAGGCGGAC
45
                    Met40
ArgProHisTyrAsnTyrTyrAlaThrLeuLeuThrLeuLeuIle
AGACCCCACTACAACTACTATGCCACACTGCTCACCCTGCTCATC
90
PheIle      50                               60
AlaValIleValPheGlyAsnValLeuValCysMetAlaValSer
GCTGTCATCGTCTTCGGCAACGTGCTGGTGTGCATGGCTGTGTCC
135
                         70
ArgGluLysAlaLeuGlnThrThrThrAsnTyrLeuIleValSer
CGCGAGAAGGCGCTGCAGACCACCACCAACTACCTGATCGTCAGC
180
              80                            90
LeuAlaValAlaAspLeuLeuValAlaThrLeuValMetProTrp
CTCGCAGTGGCCGACCTCCTCGTCGCCACACTGGTCATGCCCTGG
225
                         100
ValValTyrLeuGluValValGlyGluTrpLysPheSerArgIle
GTTGTCTACCTGGAGGTGGTAGGTGAGTGGAAATTCAGCAGGATT
270
             110                           120
HisCysAspIlePheValThrLeuAspValMetMetCysThrAla
CACTGTGACATCTTCGTCACTCTGGACGTCATGATGTGCACGGCG
315
```

Fig. 2B

```
                        130
SerIleLeuAsnLeuCysAlaIleSerIleAspArgTyrThrAla
AGCATCCTGAACTTGTGTGCCATCAGCATCGACAGGTACACAGCT
360
            140                              150
ValAlaMetProMetLeuTryAsnThrArgTyrSerSerLysArg
GTGGCCATGCCCATGCTGTACAATACGCGCTACAGCTCCAAGCGC
405
                     Ala         160
ArgValThrValMetIleSerIleValTrpValLeuSerPheThr
CGGGTCACCGTCATGATCTCCATCGTCTGGGTCCTGTCCTTCACC
450
            170                     Thr      180
IleSerCysProLeuLeuPheGlyLeuAsnAsnAlaAspGlnAsn
ATCTCCTGCCCACTCCTCTTCGGACTCAATAACGCAGACCAGAAC
495
                             190
GluCysIleIleAlaAsnProAlaPheValValTyrSerSerIle
GAGTGCATCATTGCCAACCCGGCCTTCGTGGTCTACTCCTCCATC
540
            200                              210
ValSerPheTyrValProPheIleValThrLeuLeuValTyrIle
GTCTCCTTCTACGTGCCCTTCATTGTCACCCTGCTGGTCTACATC
585
                     Lys      220
LysIleTyrIleValLeuArgArgArgArgLysArgValAsnThr
AAGATCTACATTGTCCTCCGCAGACGCCGCAAGCGAGTCAACACC
630
            230             Asn      LysThr  240
LysArgSerSerArgAlaPheArgAlaHisLeuArgAlaProLeu
AAACGCAGCAGCCGAGCTTTCAGGGCCCACCTGAGGGCTCCACTA
675
     Asp                          250
LysGluAlaAlaArgArgAlaGlnGluLeuGluMetGluMetLeu
AAGGAGGCTGCCCGGCGAGCCCAGGAGCTGGAGATGGAGATGCTC
720
            260                              270
SerSerThrSerProProGluArgThrArgTyrSerProIlePro
TCCAGCACCAGCCCACCCGAGAGGACCCGGTACAGCCCCATCCCA
765
```

Fig. 2C

```
                                      280
ProSerHisHisGlnLeuThrLeuProAspProSerHisHisGly
CCCAGCCACCACCAGCTGACTCTCCCCGACCCGTCCCACCATGGT
810
            Asn290                             300
LeuHisSerThrProAspSerProAlaLysProGluLysAsnGly
CTCCACAGCACTCCCGACAGCCCCGCCAAACCAGAGAAGAATGGG
855
          *ValAsn      Arg         310Phe
HisAlaLysAspHisProLysIleAlaLysIlePheGluIleGln
CATGCCAAAGACCACCCCAAGATTGCCAAGATCTTTGAGATCCAG
900
                320                       330
ThrMetProAsnGlyLysThrArgThrSerLeuLysThrMetSer
ACCATGCCCAATGGCAAAACCCGGACCTCCCTCAAGACCATGAGC
945
                              340
ArgArgLysLeuSerGlnGlnLysGluLysLysAlaThrGlnMet
CGTAGGAAGCTCTCCCAGCAGAAGGAGAAGAAAGCCACTCAGATG
990
                350                       360
LeuAlaIleValLeuGlyValPheIleIleCysTrpLeuProPhe
CTCGCCATTGTTCTCGGCGTGTTCATCATCTGCTGGCTGCCCTTC
1035
                              370
PheIleThrHisIleLeuAsnIleHisCysAspCysAsnIlePro
TTCATCACACACATCCTGAACATACACTGTGACTGCAACATCCCG
1080
                380                       390
ProValLeuTyrSerAlaPheThrTrpLeuGlyTyrValAsnSer
CCTGTCCTGTACAGCGCCTTCACGTGGCTGGGCTATGTCAACAGC
1125
                              400
AlaValAsnProIleIleTyrThrThrPheAsnIleGluPheArg
GCCGTGAACCCCATCATCTACACCACCTTCAACATTGAGTTCCGC
1170
              Met         414
LysAlaPheLeuLysIleLeuHisCysEnd
AAGGCCTTCCTGAAGATCCTCCACTGCTGACTCTGCTGCCTGCCC
1215
```

Fig. 2D

```
GCACAGCAGCCTGCTTTCCACCTCCCTGCCCAGGCCGGTCCAGCC
GTCACCCTTGCGAACCGTGAGCAGGAAGGCCTGGGTGGATCGGCC
TCCTCTTCACCCCGGCAGCCCTGCAGTGTTCGCTTGGCTCCATGC
TCCTCACTGCCCGCACACCCTCACTCTGCCAGGGCAGTGCTAGTG
AGCTGGGCATGGTACCAGCCCTGGGGCTCCCCCAGCTCAGGGGC
AGCTCATAGAGTCCCCCCTCCCACCTCCAGTCCCCTATCCTTGG
CACCAAAGATCGAGCCGCCTTCCTTGACCTTCCTCTGGGCTCTAG
GGTTGCTGGAGCCTGAGTCAGGGCCCAGAGGCTGAGTTTTCTCTT
TGTGGGGCTTGGCGTGGAGCAGGCGGTGGGGAGAGATGGACAGTT
CACACCCTGCAAGGCCCACAGGAGGCAAGCAAGCTCTCTTGCCGA
GGAGCCAGGCAACTTCAGTCCTGGGAGACCCATGTAAATACCAGA
CTGCAGGTTGGACCCCAGAGATTCCCAAGCCGAAAAACCTTAGCT
CCCTCCCGGCACCCCGATGTGACCTCTACTTTCCAGGCTAGTCCG
ACCCACCTCACCCCGTTACAGCTCCCCAAGTGGTTTCCACATGCT
CTGAGAAGAGGAGCCCTCATCTTGAAGGGCCAGGAGGGTCTATGG
GGAGAGGAACTCCTTGCCTAGCCCACCCTGCTGCCTTCTGACGGC
CCTGCAATGTATCCCTTCTCACAGCACATGCTGGCCAGCCTGGGG
CCTGGCATGGTAGGCTCAGTCCCTGTAACTCTATCTGGGCCTGGG
CTAGGGTACATCAGAGGTTCTTTGAGGGACTGCCTCTGCCACACT
CTGACAGCAAAACCACTTTCCTTTTCTATTCCTTCTGGCCTTTCC
TCTCTCCTGTTTCCCTTCGCTTCCACTGCCTCTGCCTTAGAGGAC
CCACGGCTAAGAGGCTGCTGAAACCATCTGGCCTGGCCTGGCCC
TGCCCTGAGGAAGGAGGGGAAGCTGCAGCTTGGGAGAGCCCCTGG
GGCCTAGACTCTGTAACATCACTATCCATGCACCAAACTAATAAA
ACTTTGACGAGTCACCTTCCCGGAATTC  2367
```

CLONED GENES FOR HUMAN DOPAMINE D2 RECEPTORS AND CELL LINES EXPRESSING SAME

This application is a division of application Ser. No. 07/413,026, filed Sep. 27, 1989, now U.S. Pat. No. 5,554,500.

This invention relates to the molecular cloning and expression of neurotransmitter receptors. In particular, it relates to transformed or transfected cells and cell lines expressing genes for a class of human dopamine D2 receptors, the proteins comprising the receptors, the DNA encoding such proteins, vectors for transforming or transfecting cells with such DNA, methods of isolating the DNA and preparing the cell lines, and methods of using the cells and cell lines.

BACKGROUND OF THE INVENTION

Neurons communicate with various target cells by the release of neurotransmitters. Neurotransmitters exert their effects by binding to sites called receptors that are located on the extracellular surface of their respective target cells. Numerous neurotransmitters have been identified, one of which is dopamine. Schizophrenia and Parkinson's disease are believed to be related at least in part to disturbances in the operation of dopamine and its receptors.

A major function of a neurotransmitter receptor is to transmit information into the interior of a target cell, causing various rapid responses of the cell. One of the major classes of receptors is known as G protein-coupled receptors. They act by coupling to a family of signal-transducing proteins located on the cytoplasmic surface of the plasma membrane. These proteins are called G proteins because they bind guanine nucleotides when activated by neurotransmitter receptors. After activation, G proteins are able to regulate a variety of cellular events, including the activity of ion channels and enzymes.

Several of the genes that code for mammalian G protein-coupled receptors have been cloned. These include the alpha-2 and beta-2 adrenergic receptors, five subtypes of muscarinic acetylcholine receptors, three subtypes of serotonin receptors, the substance K receptor, and a rat dopamine D2 receptor. All of the G protein-coupled neurotransmitter receptors cloned to date have a predicted structure having seven transmembrane domains and several regions of strong homology, suggesting that they may have arisen from a common ancestral gene.

The cloning of subtypes of some of these neurotransmitter receptors indicates a molecular basis for pharmacological heterogeneity. For example, several subtypes of muscarinic, serotonergic, and adrenergic receptors have now been cloned. See Bonner et al., *Science,* 237: 527–532 (1987); Bonner et al., *Neuron,* 1: 403–410 (1988); Peralta et al., *EMBO J.,* 6: 3923–3929 (1987); Kubo et al., *Nature,* 323: 411–416 (1986); Julius et al., *Science,* 241: 558–564 (1988); Fargin et al., *Nature,* 335: 358–360 (1988); Kobilka et al., *Science,* 228: 650–656 (1987); and Dixon et al., *Nature,* 321: 75–79 (1986), all of which are incorporated herein by reference. These receptor subtypes are expressed in distinct regions of the brain and body.

The cloning of the muscarinic acetylcholine receptors provides an example of how the general technique of homology screening was applied to the identification of a family of genes encoding a G protein-coupled receptor. See Bonner et al., *Science,* 237: 527–532 (1987) and Bonner et al., *Neuron,* 1: 403–410 (1988), both of which are incorporated herein by reference.

In the work reported in *Science,* the authors made a probe from the highly conserved transmembrane region near the 5' region of the porcine brain muscarinic receptor gene with certain modifications. The probe was used to screen a rat cerebral cortex cDNA library of clones in the pCD mammalian expression vector. The clones were characterized before isolation by using Southern blots of portions of the library. Dilutions were done to obtain a single band by Southern blotting. The cDNA inserts were transfected into mouse fibroblast (A9) or COS-7 cells. The transfected cells were assayed for the ability of the cell membranes to bind a muscarinic antagonist. The authors found four different muscarinic receptor genes.

The *Neuron* article reports the cloning and expression of the human and rat m5 muscarinic acetylcholine receptor genes in an approach similar to that in the *Science* article. A human genomic library was screened using the rat m1 receptor gene as a probe, which identified the human m5 receptor gene. The homologous rat gene was isolated from a rat genomic library, using a portion of the human gene as a probe. The coding portion of the human gene was inserted into the plasmid pCD-PS, a mammalian expression vector that utilizes an SV40 promoter, and expressed in CHO cells.

On the basis of functional and pharmacological data, central dopamine receptors have been divided into D1 and D2 subtypes. Dopamine D1 and D2 receptors stimulate and inhibit adenylate cyclase, respectively, by coupling to different G proteins. See Kebabian et al., *Nature,* 277: 93–96 (1979), incorporated herein by reference. D2 receptors are known to be abundant within various forebrain regions innervated by dopaminergic neurons projecting from the mesencephalon. See Bjorklund and Lindvall, "Dopamine Containing Systems in the CNS," in *Handbook of Chemical Neuroanatomy Vol. 2: Classical Transmitters in the CNS,* Bjorklund and Hokfelt, eds., (Elsevier, Amsterdam, 1984), pp. 55–122; Fuxe et al, "Dopaminergic Systems in the Brain and Pituitary," in *Basic and Clinical Aspects of Neuroscience,* Fluckiger et al., eds., (Springer Verlag & Sandox, Heidelberg, 1985), pp. 11–25; Anden et al., *Life Sci.,* 3: 523–530 (1964); Anden et al., *Life Sci.,* 4: 1275–1279 (1965); and Dahlstrom et al., *Acta. Physiol. Scand.,* 62: 485–486 (1964), all of which are incorporated herein by reference. D2 receptors have also been shown to be presynaptically located on dopaminergic neurons, where they modulate dopamine release. See Roth, *Ann N.Y. Acad. Science,* 430: 27–53 (1984) and White et al., *J. Pharm. Exp. Ther.,* 231: 275–280 (1986), both of which are incorporated herein by reference.

Abnormalities in central dopaminergic function have been implicated in the pathophysiology of schizophrenia and Parkinson's disease. See Stevens, *Arch. Gen. Psychiatry,* 29: 177–189 (1973); Synder, *Amer. J. Psychiatry,* 133: 197–202 (1976); and Hornykiewicz, *Wien. Klin. Wochenschr.,* 75: 309–312, all of which are incorporated herein by reference. Schizophrenia is treated with antipsychotic drugs which block central D2 receptors, and Parkinson's disease is treated by drugs which lead to their stimulation. See Baldessarini, "Drugs and the Treatment of Psychiatric Disorders," in *The Pharmacological Basis of Therapeutics,* Gilman et al., eds., (Macmillan, New York, 1985) pp. 387–445; Bianchine et al., "Drugs for Parkinson's Disease, Spasticity, and Acute Muscle Spasms," in *The Pharmacoliogical Basis of Therapeutics,* Gilman et al., eds., (Macmillan, New York, 1985) pp. 473–490; Iversen et al., *Science,* 188: 1084–1089 (1975); and Seeman et al., *Nature,* 261: 717–719 (1976), all of which are incorporated herein by reference.

Prolonged treatment with antipsychotic agents is associated with extrapyramidal (motor) side effects such as tardive dyskinesia. Since the motor side effects are believed to be mediated by receptors located within the striatum, and since antipsychotic activity is believed to be mediated by sites within limbic and cortical regions, investigation of a potential heterogeneity of D2 receptors between these brain regions has become a focus for drug development. See Borison et al., *Brain Res. Bull.*, 11: 215–218 (1983); Leonard et al., *Biochem. J.*, 248: 595–602 (1987); and Baldessarini et al.,*Annu. Rev. Neurosci.*, 3: 23–41 (1980), all of which are incorporated herein by reference.

Dopamine is the major catecholamine present in retina, where its synthesis and release is stimulated by light. Invone et al., *Science*, 202:901–902 (1978), incorporated herein by reference. As in the brain, retinal dopamine receptors have been divided into two subtypes, based on their pharmacological and functional properties. See Elena et al., *Curr. Eye Res.*, 8:75–83 (1989) and Qu et al., *J. Pharm. Exp. Ther.*, 248:621–625 (1989), both of which are incorporated herein by reference. Dopamine D1 receptors stimulate adenylate cyclase by coupling with the G-protein Gs, and D2 receptors inhibit adenylate cyclase by coupling with the G-protein Gi. Various drugs discriminate between these receptors; for example, SCH23396 has higher affinity for D1 receptors, while substituted benzamides, such as sulpiride and raclopride, have higher affinity for D2 receptors. See Qu et al., op.cit. and Hall and Wadel, *Acta Pharmacol et toxicol.*, 58:368–373 (1986), incorporated herein by reference.

A dopamine D2 receptor from rat brain was recently cloned, sequenced, and expressed. See Bunzow et al., *Nature*, 336: 783–787 (1988), incorporated herein by reference. The article reports the use of the hamster beta-2 adrenergic receptor gene as a hybridization probe to screen a rat genomic library under low stringency hybridization conditions. The authors found a clone having a fragment with a high degree of nucleotide identity to one of the transmembrane domains of the gene. This fragment was used to probe a rat brain cDNA library under high stringency hybridization conditions. A fragment of about 2.5 kB was isolated. Using this cDNA as a probe in a Northern Blot analysis of mRNA from rat brain, the authors showed that the cDNA was nearly full-length. The cDNA was determined to be 2,455 bases in length. Comparison with the genomic clone showed the presence of at least one intron in the coding region. The tissue distribution of the encoded mRNA was examined by Northern Blot analysis and found to be very similar to that for the dopamine D2 receptor. The cDNA was cloned into a eucaryotic expression vector and transfected into a mouse fibroblast cell line. Stable transfectants were isolated. The cell membranes were shown to bind a D2 ligand. The paper provided a deduced amino acid sequence for the receptor. The authors concluded that the structural features of the protein showed it to belong to the family of G protein-coupled receptors.

Prior to the present invention, the scientific literature does not report the isolation, cloning, and expression of a gene encoding a human dopamine D2 receptor. Such DNA and cell lines expressing it have several important scientific and pharmaceutical applications. First, the cloning and expression of human dopamine D2 receptor genes would permit the receptors to be studied in isolation from other related dopamine receptors.

Second, although there is substantial species homology for all of the G protein-coupled receptors that have been cloned to date, all of the receptors have differences in their predicted protein sequences. These differences are likely to translate into differences in their pharmacology. Thus, for example, it would be highly desirable to use human dopamine D2 receptors rather than the rat dopamine D2 receptors for drug development purposes.

Third, the fact that pharmacological subtypes of some of the other G protein-coupled receptors, such as the muscarinic receptor, have been found to be encoded by different genes, together with certain pharmacological data reported herein, suggests that dopamine receptors may consist of multiple genetic subtypes. Cloning and expression of the genes for those subtypes would permit the study of subtle differences in their pharmacology.

SUMMARY OF THE INVENTION

It is an object of the invention to provide a nucleic acid sequence that encodes a protein which comprises a human dopamine D2 receptor.

A further object of the invention is to provide constructs containing the genes encoding such receptors under the transcriptional and translational regulatory control of regulatory genes recognized by a desired host to which the human dopamine D2 receptor genes are foreign.

A still further object of the invention is to provide an isolated or pure clone from a human tissue DNA library, wherein the clone contains a DNA sequence that encodes a human dopamine D2 receptor.

Another object of the invention is to provide an expression vector that contains the DNA of the invention and is capable of transforming a host cell.

Still another object of the invention is to provide host cells and have been transformed with such DNA and which express a human dopamine D2 receptor.

Yet another object of the invention is to provide methods for obtaining a DNA sequence encoding a human dopamine D2 receptor, methods for preparing a cell that expresses the receptor, and methods for using such cells in the pharmacological, physiological, functional, or other investigational analysis of dopamine, dopamine receptors, and dopamine agonists or antagonists.

Additional objects and advantages of the invention will be set forth in part in the description which follows, and in part will be obvious from the description, or may be learned by the practice of the invention. The objects and advantages of the invention will be attained by means of the instrumentalities and combinations particularly pointed out in the appended claims.

To achieve the objects and in accordance with the purpose of the invention, as embodied and broadly described herein, an isolated or essentially pure DNA sequence encoding a human dopamine D2 receptor is disclosed herein. Preferably, the DNA sequence is a cDNA sequence, and most preferably it is the cDNA sequence shown in FIGS. 2A–2D or allelic variants thereof.

An alternative embodiment of the invention comprises isolated or essentially pure DNA derived from the cDNA of FIGS. 2A–2D by single or multiple mutations, including replacements, insertions, deletions, and transpositions.

The invention also provides a method of obtaining a DNA sequence encoding a human dopamine D2 receptor. One or more first DNA probes are prepared that are complementary to one or more nucleotide sequences of mRNA that encode one or more poorly conserved regions of a non-human, mammalian dopamine D2 receptor. Then one or more second DNA probes complementary to one or more nucleotide sequences of mRNA that encode one or more highly conserved regions of the receptor are prepared. A human genomic or cDNA library is screened with the probes to identify a clone that hybridizes with the probes. The human DNA sequence is recovered from the clone and evaluated to determine if it encodes a human dopamine D2 receptor.

The invention also provides a method for obtaining DNA that codes for other types or subtypes of human dopamine receptors. One or more DNA probes are prepared that are based upon a nucleotide sequence or sequences shown in the cDNA of FIGS. 2A–2D. The probe is used to screen a human genomic or cDNA library to identify clones that hybridize with it. The human DNA sequences are recovered, isolated, and sequenced. They are then compared to a cDNA sequence of FIGS. 2A–2D to identify potential candidates for other receptors. Sequences are transfected into mammalian cells that do not otherwise express a dopamine receptor, causing the cells to express the sequences. The transfected cell or part thereof that contains the protein expressed by the DNA sequence is used in an assay that identifies a dopamine receptor to identify and confirm those sequences that encode such a receptor.

The invention also provides an isolated or pure clone from a human tissue DNA library containing DNA that encodes a human dopamine D2 receptor. Preferably, the clone is from a human retinal cDNA library, and most preferably it is an essentially pure culture of bacteriophage containing the cDNA inserted into the genome.

The invention also provides sequencing and expression vectors, wherein the DNA of the invention is inserted into the vector in proper orientation and correct reading frame and in conjunction with the appropriate regulatory sequences.

The invention further provides a procaryotic cell transformed by the DNA of the invention or a mammalian cell or cell line transfected with the DNA and expression vector of the invention. The mammalian cell line is capable of continuous growth in a suitable culture medium. Preferably, it is a neuronal or fibroblast cell line.

The invention provides methods for using the cells and cell lines for the pharmacological, physiological, functional, or other investigational analysis of dopamine, dopamine agonists, or dopamine antagonists. A preferred method of analysis of antagonists is an in vitro method of determining the ability of a chemical to bind to a human dopamine D2 receptor. The chemical is contacted with a transfected mammalian cell or part thereof expressing the receptor and the ability of the cell or part thereof to bind the chemical is determined. A preferred method of analysis of agonists is an in vitro method of determining the ability of a chemical to change levels of second messengers within the transfected cell grown in culture. A preferred measure is cyclic AMP (cAMP) levels.

The accompanying figures, which are incorporated in and constitute a part of the specification, illustrate an embodiment of the invention and, together with the description, serve to explain the principles of the invention.

BRIEF DESCRIPTION OF THE DRAWINGS

FIGS. 2A–2D. Sequence map of human retinal dopamine D2 receptor cDNA and designated amino acid sequence with comparison to published rat dopamine D2 receptor designated amino acid sequence. Numbers of nucleotides are indicated below the sequences in italics, and the amino acids are numbered above. Where the human and rat amino acids differ, the human amino acid is underlined, and the rat substitution is indicated above. The asterisk indicates the position of an extra isoleucine in the rat sequence.

| inhibitor | k | n |
|---|---|---|
| (□) chlorpromazine | 0.0015 ± 0.13 | 0.9 ± 0.1 |
| (○) (−)sulphride | 0.046 ± 0.02 | 1.2 ± 0.2 |
| (■) apomorphine | 0.25 ± 0.03 | 1.0 ± 0.1 |
| (●) (+)sulphride | 5.45 ± 1.08 | 1.0 ± 0.1 |
| (□) dopamine | 24.8 ± 8.17 | 1.1 ± 0.1 |

Figure 4:
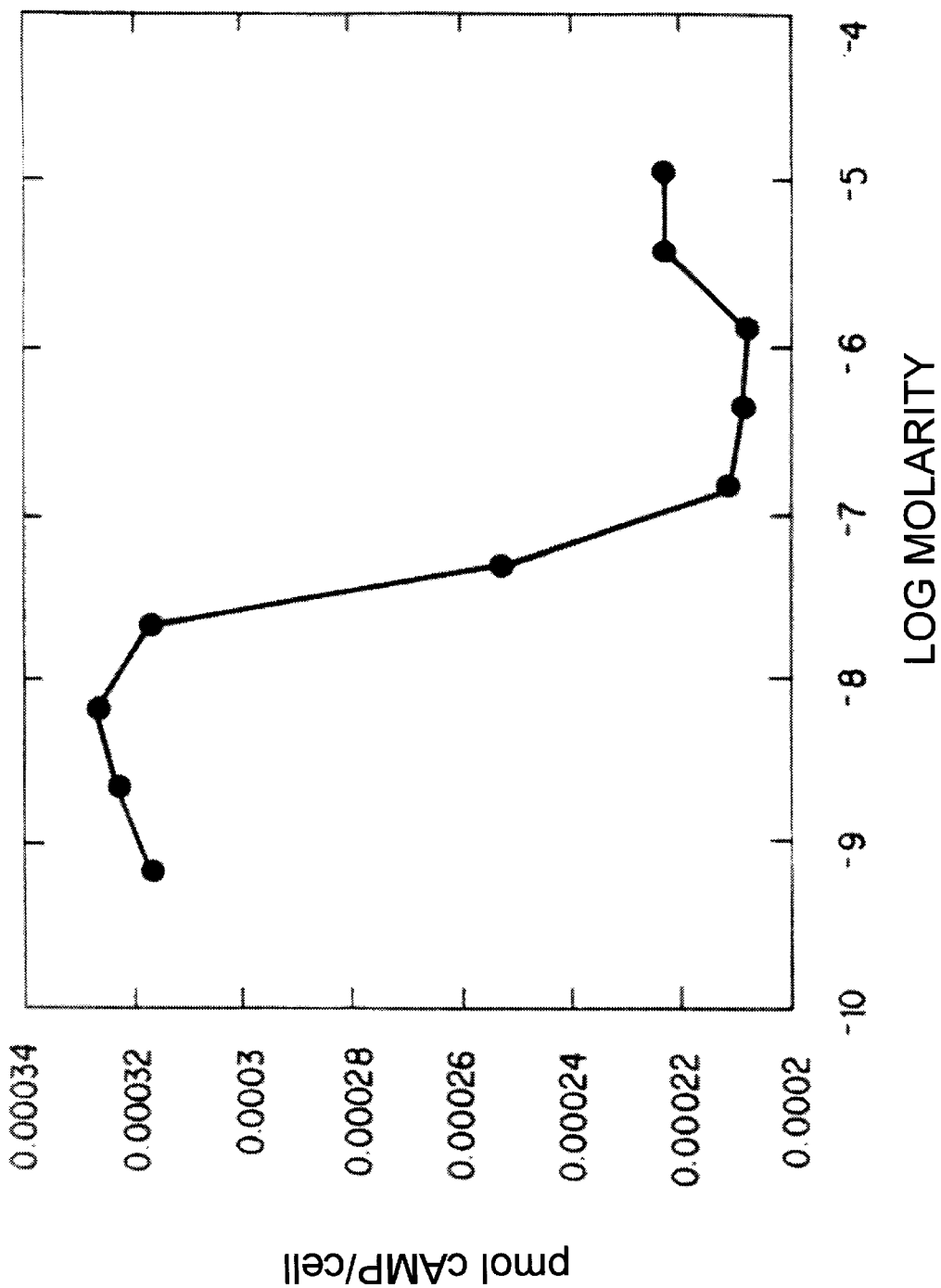

FIG. 4. Changes in cAMP levels in transfected A9 L cells. Dopamine D2 receptors expressed by A9 L cells decrease cAMP levels. A9 L cells which express ~500 fmole/mg proteins $^3$H-raclopride binding sites were incubated with increasing concentrations of dopamine for 10 min. cAMP levels were determined by radioimmunoassay.

DESCRIPTION OF THE PREFERRED EMBODIMENTS

Reference will now be made in detail to the presently preferred embodiments of the invention, which, together with the following examples, serve to explain the principles of the invention.

The invention relates to cells and cell line s transformed or transfected with and expressing DNA that codes for a human dopamine D2 receptor. As used herein, a dopamine D2 receptor is a site located on the extracellular surface of a cell that binds dopamine and certain drugs, such as sulpiride and raclopride. See Kebabian and Calne, *Nature (London)*, 277:93–96 (1980) and Hall and Wadel, *Acta Pharmacol et toxicol.*, 58:368–373 (1986), both of which are incorporated herein by reference.

As explained in greater detail in Example 1, we found evidence for a heterogeneity of dopamine D2 receptors, based on ligand binding data. Such data indicates that high concentration of D2 receptors are present in retinal photoreceptors. However, in our experiments with both monkey and rat retina, we failed to detect mRNA within photoreceptors. The most likely explanation for this observation is that photoreceptors express dopamine D2 receptors that are encoded by a different gene. Thus, this invention is not limited to DNA encoding any one particular D2 receptor subtype or cell lines expressing the same. Given the teachings disclosed herein, a person skilled in the art will be able to clone and express other D2 subtypes.

The DNA of the invention is an isolated or essentially pure DNA sequence (i.e., polydeoxyribonucleotide) encoding a protein which comprises a human dopamine D2 receptor. As used herein, the term "isolated" and variations thereof means that the DNA is in isolation from DNA encoding proteins normally accompanying these receptors or encoding a different dopamine receptor. Thus, the DNA of the invention includes DNA encoding a D2 receptor when that DNA has been cloned into a bacterial vector, such as a plasmid, or into a viral vector that may be harbored by a bacteriophage, provided that such clones are isolated from clones that contain DNA encoding other proteins normally accompanying such receptors or encoding a different dopamine receptor. As used herein, the term "essentially pure" and variants thereof means the DNA is substantially free of DNA and RNA that does not encode a human dopamine D2 receptor. That is, there will be no more than about 0.1 percent of other DNA and RNA and preferably no more than about 0.01 percent of other DNA and RNA in any sample that contains the DNA encoding the D2 receptor.

Preferably, the DNA of the invention is a complementary DNA (cDNA). FIGS. 2A–2D show the nucleotide sequence of a particularly preferred embodiment of the invention. The cDNA is approximately 2.5 kilobases in length. It codes for a protein with the deduced amino acid sequence shown in FIGS. 2A–2D. The protein contains seven predicted transmembrane regions. They consist of the seven amino acid sequences comprised of the amino acids 38–60, 72–97, 109–130, 152–174, 187–210, 345–368, and 377–400, coded for by the nucleotide sequences comprised of the nucleotides 111–179, 213–290, 324–389, 453–521, 558–629, 1032–1103, and 1128–1198, respectively, as shown in FIGS. 2A–2D.

The cDNA shows substantial homology with the cDNA isolated from rat brain and published in Bunzow et al., op. cit. The homology is 90% at the nucleotide level in the 5' untranslated and coding regions of the cDNA. Comparison of deduced amino acid sequences of the two proteins indicates the presence of 18 amino acid substitutions.

The DNA of the invention may be obtained by various methods involving known molecular biology techniques based on homology screening that have been modified and applied in accordance with the discoveries and teachings described herein.

In a preferred embodiment, one or more DNA probes are prepared that are complementary to one or more regions of mRNA (i.e., one or more polyribonucleotides) that encode one or more poorly conserved regions of a non-human, mammalian dopamine D2 receptor, such as a rat D2 receptor. Preferably, the probes are complementary to regions of the mRNA that encode the n-terminal and c-terminal of the D2 receptor as well as to a region that encodes one of the cytoplasmic loops that are known to be poorly conserved. As used herein, the term "poorly conserved" refers to regions of the dopamine D2 receptor that are not similar in sequence to the sequences of the other G-protein coupled receptors. A second set of one or more DNA probes is also prepared, with each probe being complementary to a region of the mRNA that encodes a highly conserved region of the D2 receptors. Such regions include those that encode the transmembrane domains of the receptor, preferably the second and third transmembrane regions. As used herein, the term "highly conserved" refers to regions of the dopamine D2 receptor that are similar in sequence to the sequences of the other G-protein coupled receptors. For example, the human dopamine D2 receptor and the beta adrenergic receptor have 62% nucleic acid identity in the region of the TM2 and TM3 probes referred to in Example 1.

The two sets of probes are used to screen a library containing DNA from human tissue that contains dopamine D2 receptors. The library may be a genomic or cDNA library. Preferably, the library is a cDNA library rather than a genomic library. A cDNA library will be easier to work with if the gene contains introns. On the other hand, a genomic library may be preferable to work with if the gene does not contain introns and if the human control sequences are desired. In addition, it is generally much more difficult to obtain cDNA libraries based on human tissue that contains D2 receptors because of the difficulty of obtaining such tissue in non-degraded form.

The library comprises DNA from human cells that express D2 receptors that have been cloned into vectors. Different segments or fragments of the DNA will have been operably and recoverably inserted into each vector so that each vector contains only one segment of the DNA. The vectors may be plasmids or viruses. If necessary because of the type of library being used, the segments of DNA will have been inserted into the vectors in a manner that they will be expressed under appropriate conditions (i.e., in proper orientation and correct reading frame).

Most preferably, the library is a lambda gt10 library that contains cDNA derived from human retina mRNA. Such a library is disclosed in Nathans and Hogness, *Cell,* 34:807 (1983), which is incorporated herein by reference.

The first set of probes would be expected to hybridize with the human homolog of the rat D2 dopamine receptor cDNA, and the second set of probes would be expected to hybridize with other related G-protein coupled receptor cDNAs as well as the human homolog of the rat D2 dopamine receptor cDNA. Therefore, clones that hybridize to both sets of probes would be expected to contain DNA encoding all or a part of a human dopamine D2 receptor. Such clones are identified and isolated by known techniques. In the case of a lambda gt10 library, such isolation comprises dilution of the plaques identified by the probes and rescreening with the probes until all plaques hybridize with the probes. The purified plaques are then rescreened with the probe that is complementary to the 5' region of the mRNA, which codes for the n-terminal region of the polypeptide, to identify those plaques most likely to contain a complete or substantially complete DNA sequence. Such clones may be further evaluated by such techniques as Northern blotting to determine if they are relatively complete and to gain an indication of whether they encode a D2 receptor.

Thus, the present invention encompasses an isolated or purified clone from a human tissue DNA library, which clone contains a DNA molecule encoding a human dopamine D2 receptor. Preferably, the clone comprises an essentially pure culture of bacteriophage containing the cDNA of FIGS. 2A–2D inserted into the genome of the phage. That is, none of the phage in the culture contains any cDNA other than the cDNA of FIGS. 2A–2D. Most preferably, the clone is the clone lambda 16A, identified in Example 1. Alternatively, the clone comprises an essentially pure culture of bacteria, such as *E. coli,* containing the cDNA of FIGS. 2A–2D inserted into a plasmid, such as pUC-18, in the bacteria. That is, none of the bacteria in the culture contain any cDNA other than the cDNA of FIG. 2.

The DNA sequences from the clones identified by the probes are recovered and evaluated by known techniques to determine if they encode a human dopamine D2 receptor. There are two principal means by which the sequence is evaluated. First, the nucleotide sequence is determined by known sequencing techniques. Preferably, this involves subcloning the DNA into a sequencing plasmid and determining the sequences of both strands of the DNA by the dideoxy chain-termination method of Kraft et al., *Biotechniques*, 6:544–546 (1988), which is incorporated herein by reference. The sequence is compared to the non-human dopamine D2 receptor sequence to determine similarities and differences. The deduced amino acid sequence is also determined and compared to the amino acid sequence for the non-human receptor. Sufficient homology permits a tentative conclusion that it is a human dopamine D2 receptor.

The isolated DNA is then preferably used to transfect a mammalian cell that does not otherwise express the receptor to cause the cell to express the DNA. The cells or parts thereof are used in known assays that identify dopamine D2 receptors to determine if the transfected cell is expressing the DNA sequence. Such assays include the use of substituted benzamides, such as $^3$H-raclopride as described in Kohler et al., *Biochemical Pharmocology*, 34: 2251–2259 (1985), incorporated herein by reference.

The DNA of the invention can be used to transform procaryotic cells, such as bacteria, fungi, or other microorganisms, or transfect eucaryotic cells, such as yeast or mammalian cells. Transformation or transfection is accomplished by techniques known in the art applied in conjunction with the discoveries and teachings disclosed herein. Such techniques include those disclosed in U.S. Pat. Nos. 4,810,648 issued Mar. 7, 1989 to Stalker, 4,766,075 issued Aug. 23, 1988 to Goeddel et al., 4,757,006 issued Jul. 12, 1988 to Toole, Jr. et al., and 4,704,362 issued Nov. 3, 1987 to Itakura et al., all of which are incorporated herein by reference.

The DNA of the invention may be joined to a wide variety of other DNA sequences for introduction into an appropriate host cell. The companion DNA will depend upon the nature of the host, the manner of introduction of the DNA into the host, and whether episomal maintenance or integration is desired. Mammalian cells are the preferred host.

Generally, DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed or transfected by the vector. Therefore, it will be necessary to select for transformed or transfected host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform or co-transfect the desired host cell.

The preferred expression vector for use in the invention is the plasmid pCD-PS. This plasmid can be prepared from the expression vector pCD according to the techniques of Bonner et al., *Neuron*, 1: 403–410 (1988), which is incorporated herein by reference. The latter plasmid is generally available to persons skilled in the art. The preferred expression vector of the invention is particularly useful for transfecting COS-7 cells.

After the modified expression vector has been prepared, it is transfected into a mammalian cell, using techniques known in the art and the teachings contained herein. The mammalian cell may be any one that can be transfected with the DNA of the present invention. Such a cell can be one that already endogenously expresses the human dopamine D2 receptor if, for example, it were desired to obtain a higher degree of expression. In addition, the cell can be one which is not stably transfected, such as a COS-7 cell. COS-7 cells express high levels of the DNA of the invention when transfected with the preferred expression vector of the invention and, therefore, are useful in assays that show quickly whether or not a particular piece of DNA transfected into the cell encodes a D2 receptor.

Preferably, the cell is one that does not otherwise express a human dopamine D2 receptor and further is one that can be stably transfected with the DNA so that the DNA is integrated into the genome and expressed on an essentially continuous basis in the cell or its progeny. Further, the cell to be transfected is preferably one from a mammalian cell line that is capable of continuous growth in a suitable culture medium. Preferred types of cell lines include those derived from neuronal cells, such as the type of pheochromocytoma cells known as PC 12 cells, fibroblast cells, such as A9 L cells, epithelial-like cells, such as Chinese hamster ovary (CHO) cells, and a glial or glial-like cells, such as c6 glioma cells. A9 L and CHO cells are useful because they have been well characterized in the case of expression of muscarinic receptors. The glioma cells are expected to be useful because they have a phenotype related to glial cells, which will be important if D2 receptors are shown to be expressed in glial cells endogenously. They would better approximate the endogenous phenotype and, therefore, better approximate the pharmacology which would be observed in the human brain. It is expected that the agonist, but not the antagonist, pharmacology of the D2 receptor will vary as a function of cell phenotype. The pheochromocytoma cells are useful because they have many properties that are similar to that of the neurons where dopamine receptors are endogenously expressed.

After transfection, the cells are evaluated by screening to identify and isolate those that have taken up the expression vector. Preferably, the expression vector will be stably inserted into the genome of the cell. If the stably transfected cells were originally from a continuous cell line, the cell can be clonally expanded to provide a cell line that is capable of continuous growth in a suitable culture medium and which expresses a human dopamine D2 receptor.

Having the cDNA sequence of the most preferred embodiment of this invention as shown in FIGS. 2A–2D, a person skilled in the art can obtain the genomic DNA that encodes the receptor shown in FIGS. 2A–2D and can also obtain the cDNA and genomic DNA for other subtypes of D2 receptors. One or more probes can be constructed, based upon the sequence information provided by FIGS. 2A–2D. The probe may be comprised of a nucleotide sequence substantially identical to the cDNA sequence of FIGS. 2A–2D, or it may be a collection of oligodeoxynucleotide probes to various regions of the cDNA as taught herein. The probes can be used under conditions of appropriate stringency to identify a sufficient number of clones from an appropriate human genomic or cDNA library so that at least one of such clones would contain the DNA encoding the receptor shown in FIGS. 2A–2D or the cDNA encoding other human dopamine D2 receptor subtypes. Clones identified by the probes would be isolated, and the DNA or cDNA inserts would be removed. The inserts would be sequenced for purposes of comparing them to the cDNA sequence of FIGS. 2A–2D. A tentative conclusion could be made as to whether DNA from a genomic library was the actual gene for the receptor shown in FIGS. 2A–2D or whether cDNA from a cDNA library encoded another D2 receptor. This conclusion could be confirmed by transfecting a mammalian cell that does not otherwise express human dopamine D2 receptors with the sequence as described herein and evaluating the transfected cell in an assay that identifies a dopamine D2 receptor. The cDNA sequences that encode other D2 receptor subtypes and obtained as outlined above can also be used to make probes for screening a human genomic library to obtain the actual genes.

Accordingly, the present invention includes isolated or essentially pure genomic DNA that encodes the receptor shown in FIGS. 2A–2D, cDNA that encodes other human dopamine D2 receptor subtypes, the genomic DNA for such subtypes, and isolated clones containing such cDNA or DNA.

Within particular D2 receptor subtypes, one might expect naturally occurring allelic variations due to natural mutations. Such mutants and variants can be identified by the techniques disclosed herein and, accordingly, are within the scope of the invention.

In addition, cDNAs isolated from libraries can differ in several ways that may be trivial with respect to the biology and pharmacology of the encoded receptors. The cDNAs may vary with respect to the length of their 5' and 3' ends; these differences are largely due to artifacts in the construction of the particular cDNA library and will not effect the encoded protein. Second, non-functional portions of the protein may be changed by alternative splicing of the parent mRNA. In general, for other G protein-coupled receptors that are homologous to the D2 receptor, the hydrophobic or transmembrane portions of the receptor and adjacent residues are important biologically. See Dixon et al., *Nature*, 326:73–77 (1987), incorporated herein by reference. The receptors that are identical or are substantially identical to the receptor shown in FIGS. 2A–2D with respect to hydrophobic transmembrane domains, but differ with respect to hydrophilic regions, such as the third cytoplasmic loop, are unlikely to functionally differ from the receptor reported herein. In the case of the receptor reported herein, it is believed that the transmembrane regions are primarily responsible for binding dopamine. Accordingly, such modified cDNAs are within the scope of the invention.

Having the cDNA of FIGS. 2A–2D, a person skilled in the art, using known techniques and the teachings disclosed herein, can prepare operable derivatives to the cDNAs and the DNAs of the invention. For example, site directed mutagenesis, as described in Botstein and Shortle, "Strategies and Applications of In Vitro Mutagenesis," *Science*, 229:1193–1210 (1985), which is incorporated herein by reference, can be applied to the cDNA of FIGS. 2A–2D to derive variants thereof. Such variants can be evaluated by the techniques described herein to determine whether or not they encode a D2 receptor. Additional techniques may be applied to the cDNA of FIGS. 2A–2D in order to create single or multiple mutations. Such mutations include replacements, insertions, deletions, and transpositions as described in Botstein and Shortle, op.cit.

Accordingly, the present invention encompasses isolated or essentially pure DNA that: 1) codes for a polypeptide having the same or enhanced biological activity as the polypeptide of FIGS. 2A–2D; 2) exhibits at least 95% homology with DNA comprising the nucleotide sequence shown from 0 to 1241 in FIGS. 2A–2D; 3) exhibits at least 99% homology within its transmembrane encoding regions with the transmembrane encoding regions of the cDNA of FIGS. 2A–2D; 4) encodes a polypeptide having transmembrane regions that exhibit at least 99% homology with the transmembrane regions of the polypeptide shown in FIGS. 2A–2D; 5) encodes a polypeptide that exhibits at least 95% homology with the polypeptide shown in FIGS. 2A–2D; or 6) hybridizes with the cDNA sequence of FIGS. 2A–2D under conditions of high stringency.

A person skilled in the art, using known techniques and the teachings disclosed herein, can use the naturally variant or derived DNA of the invention to prepare sequencing vectors, expression vectors, transformed or transfected cells, and transfected cell lines as disclosed herein. Accordingly, these are within the scope of the present invention.

The primary utility for the cells and cell lines of the present invention is in the development of better drugs for the treatment of Parkinson's disease and schizophrenia, and the primary utility for the DNA, clones, and vectors of the present invention is for the construction of such cells and cell lines.

Cells and cell lines that express human dopamine D2 receptors, particularly those that express an individual subtype, will be extremely useful in the study of receptor function and its implications in Parkinson's disease and schizophrenia. Relative to animal models, such cell culture assays are quick, inexpensive, and highly standardized. In addition, the cloned DNA sequences can be used to measure the mRNAs that encode these receptors, thus measuring tissue specific expression. Moreover, receptor pharmacology can be determined in isolation from other related receptors, including different dopamine receptor types or subtypes. Therefore, these assays will be tools in the effort to provide a scientific basis for the rational development to new drugs.

In addition, the assays have direct and immediate pharmacological utility. They can be used to screen drugs in order to find or develop dopamine antagonists (substances that block the receptors) or agonists (substances that stimulate the receptors). Generally known techniques, modified in accordance with the discoveries and teachings disclosed herein, can be used with the cells and cell lines of the invention to evaluate potential antagonists or agonists by generating dose response, saturation, inhibition, or displacement curves. Initial candidates can be further tested for specificity, binding affinity, and activity.

Figure 3:
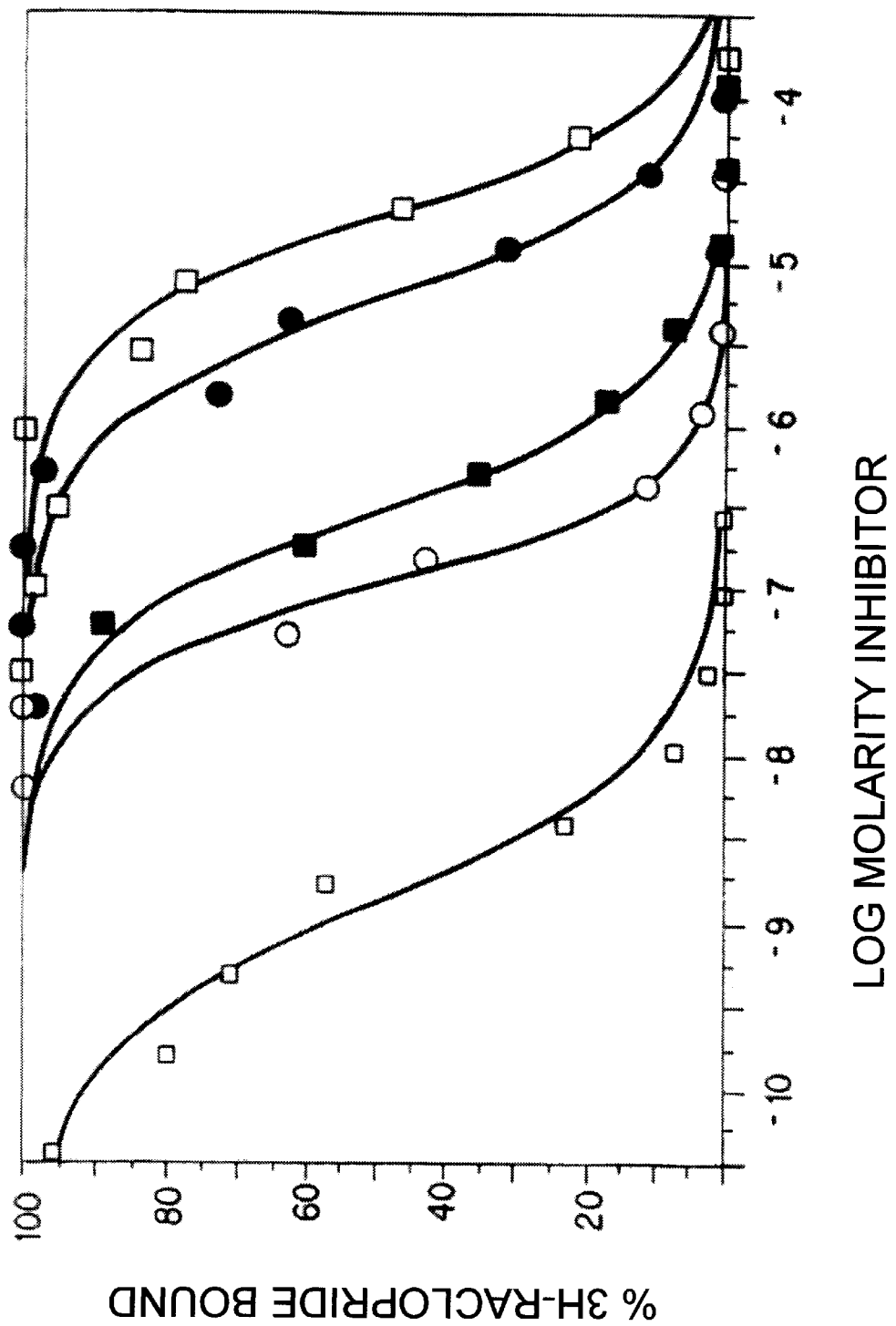
FIG. 3. Pharmacological analysis of sites labeled by $^3$H-raclopride in COS-7 cells. Sites were labeled with 0.7 nM of $^3$H-raclopride and nonspecific binding was defined with 1 uM chlorpromazine. Lines indicate best fits of the data to the function $y=100-100x^n/k/(1+x^n/k)$ where x=inhibitor concentration, n=hill number, k=inhibition constant, and y=% $^3$H-raclopride bound. These parameters for each of the inhibitors are as follows.

Whether or not a chemical binds to a human dopamine D2 receptor can be determined by contacting the chemical with a cell or a part thereof from a host cell transformed by the DNA of the invention and determining the ability of the cell or part thereof to bind to the chemical in the appropriate assay in the presence of a chemical known to bind to a D2 receptor, such as raclopride. FIG. 3 illustrates the utility of the cells of the invention in determining an antagonist.

Since agonists also bind to receptors, a human dopamine D2 receptor agonist needs to be identified in a functional assay. Such assays include the so-called second messenger assays. When neurotransmitters bind to receptors on the surface of cells, the metabolism of the various molecules is altered. When these molecules effect the physiology of the cell, they are referred to as second messengers. Two second messenger pathways that have been well characterized are inositol phosphate and cyclic adenosine monophosphate (cAMP) metabolism. See Berridge, *Annu. Rev. Biochem.*, 56:159 (1987) and Gilman, *Annu. Rev. Biochem.*, 56:615 (1987), both of which are incorporated herein by reference. cAMP metabolism can be examined by various methods. The activity of the enzyme adenylate cyclase or the levels of cAMP can be measured.

Thus, the invention provides an in vitro method for evaluating a chemical to determine if it is a dopamine D2 receptor agonist. The chemical is contacted with a cell transformed by the DNA of the invention. The effect of the chemical on a second messenger pathway of the cells is then measured. FIG. 4 illustrates the utility of the cells of the invention in determining an agonist.

Cells and cell lines expressing human dopamine D2 receptors would provide a sufficient amount of the proteins for the preparation of antibodies. The antibodies can be used to define more clearly the localization of receptor types than is possible using in situ hybridization to mRNA. They could also be used for diagnostic purposes if clinically significant abnormalities were found in any of the receptor subtypes. Moreover, they would permit purification of the receptor proteins by affinity chromatography. Purified D2 receptor subtypes would permit the 3-dimensional protein to be studied by X-ray crystallography. This information would be useful in rational drug design.

It is to be understood that application of the teachings of the present invention to a specific problem or environment will be within capabilities of one having ordinary skill in the art in light of the teachings contained herein. Examples of the products of the present invention, processes for their production, and processes for their use appear in the following examples.

EXAMPLE 1

Molecular Cloning and Expression of a Human Dopamine D2 Receptor

A dopamine D2 receptor from rat brain was recently cloned, sequenced and expressed. Bunzow, op.cit. Using northern blot analysis, mRNA encoding this receptor was observed in various brain regions known to contain D2 receptors. Using in situ hybridization histochemistry, mRNA encoding this receptor has recently been shown to be expressed by cells which are both pre- and post-synaptically located with respect to three major ascending dopaminergic pathways, e.g., the nigrostriatal, mesolimbic and mesocortical pathways. Weiner and Brann, *FEBS Letters*, 253:207–213 (1989), incorporated herein by reference. To examine if this gene accounts for the known distribution of D2 receptors within the retina, we localized mRNA within rat retina using oligodeoxynucleotide probes directed to the rat sequence. Since these probes were also able to detect mRNA in monkey retina, indicating homology within the probes to primate mRNA, we used these probes to screen a human retinal cDNA library. A human retinal cDNA was cloned, sequenced and expressed in mammalian cells.
Materials and Methods Preparation of oligodeoxynucleotides. Five oligodeoxynucleotide probes were prepared on an Applied Biosystems automated DNA synthesizer (courtesy of P. Keller, LMG, NINDS) and purified by preparative gel electrophoresis. The sequence of the probes were complementary to bases 4–51 (S1: 5'-GTT CTG CCT CTC CAG ATC GTC ATC GTA CCA GGA CAG GTT CAG TGG ATC-3'), bases 954–1001 (S2: 5'-CAG GAC CTT GTT CTG CTG CTC CAG CTC GTG CAC GCG CTC GAT GAA GCT-3') bases 1198–1245 (S3: 5'-GCA GTG CAA GAT CTT CAT GAA GGC CTT GCG GAA CTC GAT GTT GAA CCT-3'), bases 217–267 (TM2: 5'-CGG CAT TAC CAG TGT GGC CAC CAG AAG ATC AGC CAC AGC AAG GCT GAC TAT-3'), and bases 352–400 (TM3: 5'-GTA CCT GTC AAT GCT GAT GGC ACA CAG GTT CAG GAT GCT TGC TGT GCA-3'). Probes S1, S2, and S3 are complementary to regions of the mRNA which encode the n-terminal, third cytoplasmic loop, and c-terminal of the rat D2 receptor, respectively. Probes TM2 and TM3 are complementary to regions of the mRNA which encode the second and third transmembrane domains of the receptor. The probes were labeled by tailing the 3' ends with terminal deoxynucleotide transferase (BRL) using $^{35}$S-alpha-dATP as a substrate for those to be used for in situ hybridizations and $^{32}$P-alpha-dATP for those to be used for northern blots. For library screening, the probes were labeled by phosphorylating the 5' ends with polynucleotide kinase using $^{32}$P-gamma-ATP as a substrate.

Northern blot analysis. Tissues were dissected from male Sprague-Dawley rats and frozen on powdered dry ice. RNA was extracted using a guanidinium isothiocyanate method. Chomczynski and Sacchi, *Anal. Biochem.*, 162:156–159 (1987), incorporated herein by reference. Fifteen ug of total RNA was run on each lane of a formaldehyde containing agarose gel and transferred to Genescreen (NEN). Blots were prehybridized for >2 hrs in hybridization buffer (4× SSPE, 50% formamide, 1× Denhardt's, 250 ug/ml sheared salmon sperm DNA) and hybridized at 37° C.>18 hrs with 9×10$^6$ DPM of a mixture of the S1, S2, and S3 probes. Denhardt's solution is 0.02% Ficoll, 0.02% bovine serum albumin, 0.02% polyvinylpyrrolidone, and 1× SSPE is (in mM: NaCl 180, NaH$_2$PO$_4$10, EDTA 1). Blots were washed 4×15 min. at 55° C. and 2×30 min. at room temperature in 1× SSPE and exposed to x-ray film for 4 days with intensification screens. Sizes of bands were estimated by comparison with standards (BRL).

In situ hybridization histochemistry. Eyes were removed from male Sprague-Dawley rats and frozen whole on dry ice. Retinas from the eyes of Rhesus monkeys (courtesy of Dr. G. Chader, NEI) were dissected, mounted flat in embedding medium and frozen on dry ice. Twelve um cryostat sections were prepared (perpendicular to the surface of the retina in each case) and thaw mounted on gelatin coated slides. Nine×10$^6$ DPM of a mixture of the S1, S2, and S3 probes were applied to each section in 50 ul of hybridization buffer (4× SSC, 50% formamide, 1× Denhardt's, 250 ug/ml sheared single stranded salmon sperm DNA, 100 mM dithiothreitol, 10% dextran sulfate). Sections were incubated for >18 hrs. in a humid chamber at 37° C. Sections were washed at 4×15 min. at 37° C. and 2×30 min. at room temperature in 1× SSC (in mM: NaCl 150, NaCitrate 15). mRNA was autoradiographically localized by dipping the sections in emulsion (NTB3, Kodak, 1:1 with water) and exposing them for two weeks. Cells were then counterstained with cresyl violet.

Screening of the Human Retinal Library. The clone lambda 16A was isolated from a human retinal lambda gt10 cDNA library obtained from Dr. J. Nathans (Johns Hopkins University School of Medicine, Baltimore). The library is described in Nathans and Hogness, op. cit. Approximately 1×10$^6$ plaques were lifted in duplicate onto Hybond-N nylon filters (Amersham). One set of filters was screened with a mixture of the S1, S2, and S3 deoxyoligonucleotide probes, and the duplicate set of filters was screened with a mixture of the TM2 and TM3 probes. Hybridizations were carried out at 42° C. in 20% formamide (vol/vol), 1 M NaCl, 50 mM Tris-HCl (pH 7.5), 5× concentrated Denhardt's solution, 0.5% SDS containing 100 ug of salmon sperm DNA per ml. The filters were washed 2×15 min. at room temperature and 2×1 hr. at 47° C. in 1× SSPE, 0.5% SDS. Clones that hybridized with both mixtures of probes were plaque purified and rescreened with the S1 probe alone to identify those most likely to be full length.

Sequence Determination. The 2.5 Kb EcoRI insert of lambda 16A was subcloned into the EcoRI site of the Bluescript II KS+ plasmid (Stratagene, catalog number 212207). The nucleotide sequences of the cDNA were determined by the dideoxy chain-termination method using synthetic 17-mers derived from the rat receptor and obtained human D2 receptor sequences as primers for double stranded plasmid sequencing. Kraft et al., *Biotechniques.*, 6:544–546 (1988), incorporated herein by reference.

Expression and Transfection. The 2.5 Kb EcoRI insert was subcloned into the pCD-PS expression vector (Bonner et al., op.cit.) and plasmid DNA was purified by using two cesium chloride gradients. COS-7 cells were plated at a density of $1 \times 10^6$ cells/10 cm dish. One to two days after plating, cells were transfected with 16A-pCD-PS DNA using a modification of the calcium phosphate precipitation procedure. Chen and Okayama, *Mol. Cell. Biol.*, 7:2745–2752 (1987), incorporated herein by reference.

Radioligand binding. Cells were scraped 48–72 hours after transfection into 10 ml of PBS/10 cm dish and pelleted at 1000× g. Cells were resuspended in 10 mM Tris, 1 mM EDTA, 5 mM $MgCl_2$ and homogenized with a polytron (Brinkman). A total particulate fraction was prepared by centrifugation at 45,000× g for 15 min. Membranes were resuspended in binding buffer (in mM: Tris-HCl 50, NaCl 120, $MgCl_2$ 1, $CaCl_2$ 1, KCl5, ascorbic acid 5.7, pH 7.4) with about 10 ug protein/tube, 0.4 ml/tube. Reactions were initiated by addition of 0.4 ml of tissue in binding buffer to 0.1 ml of drugs. For saturation experiments, increasing concentration of $^3$H-raclopride (NEN) and $^3$H-SCH23396 (NEN) were incubated with membranes for 30 min at 30° C. Nonspecific binding was defined with 1 uM chlorpromazine. Reactions were terminated by filtering membranes through Whatman GFC filters using a cell harvester (Brandel). Data were analyzed by nonlinear regression on a VAX II computer using the program DATAPLOT (distributed by the National Technical Information Service). For saturation experiments, the data were fit to the equation $y = ax^n/k/(1+x^n/k)$ where y=ligand bound, x=ligand concentration, a=maximal number of binding sites, n=hill number, and $k=k_D$. For inhibition experiments, the data were fit to the equation $y = 100xn/k/(1+xn/k)$ where y=% inhibition, x=concentration of inhibitor, and k=inhibition constant.

Results

Distribution of retinal D2 receptor mRNA. Since the n-terminal, c-terminal, and third loop of the dopamine D2 receptor diverge in sequence from all other G-protein coupled receptors which have been cloned to date, probes (S1, S2, and S3), which are complementary to a portion of these regions, were used to localize mRNA to ensure specificity. The specificity of the probes were verified based on three criteria. First, when the three probes are used for in situ hybridization histochemistry in adjacent sections of rat brain, they label identical patterns of hybridization, and the intensity of hybridization is additive when the probes are combined. Second, on northern blots of various brain regions, including striatum, cerebral cortex, hippocampus, and brainstem, these probes label mRNA with a size of 2.6 kB, a size which is identical to that observed with a long probe cloned from the rat brain cDNA. Third, the pattern of hybridization observed in retina with these probes is distinct from that observed for other probes which are chemically similar, i.e., those for tyrosine hydroxylase, rhodopsin and transducin.

Figure 1A:
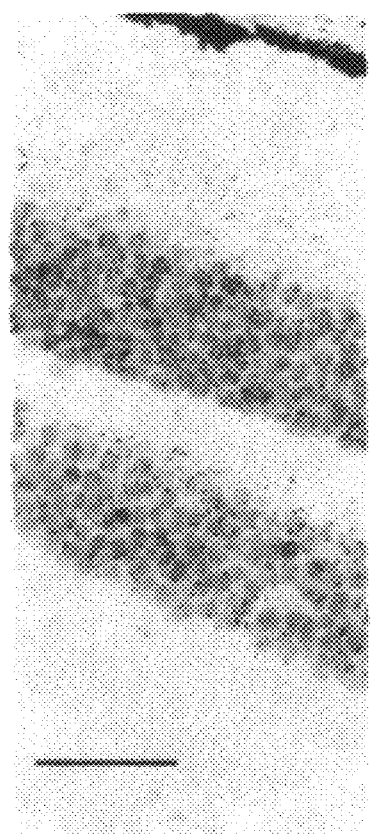
FIGS. 1A–1D. Localization of D2 receptor mRNA in rat and monkey retina by in situ hybridization histochemistry. Brightfield (FIG. 1A and FIG. 1C) and darkfield (FIG. 1B and FIG. 1D) photomicrographs of 12 um sections of rat (FIG. 1A and FIG. 1B) and monkey (FIG. 1C and FIG. 1D) retina. Bars are 50 um. Abbreviations: PE pigment epithelium, OS outer segment, IS inner segment, ONL outer nuclear layer, OPL outer plexiform layer, INL inner nuclear layer, IPL inner plexiform layer, and GCL ganglion cell layer.
Figure 1B:
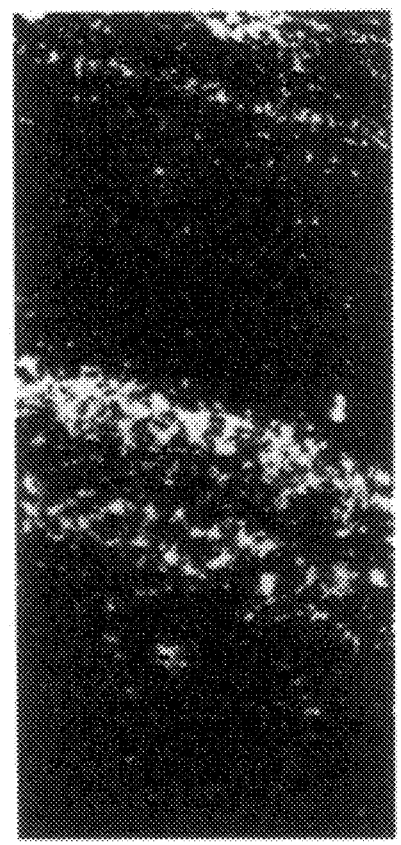
Figure 1C:
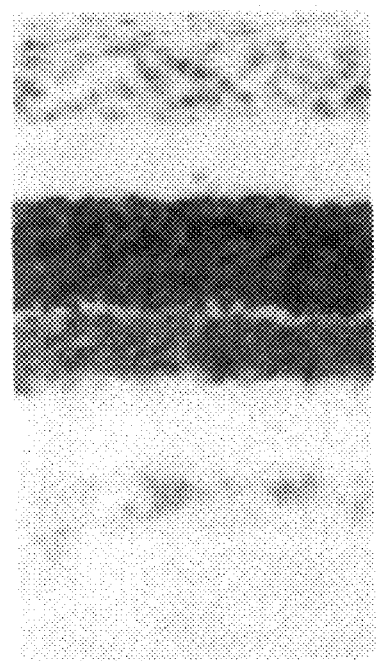
Figure 1D:
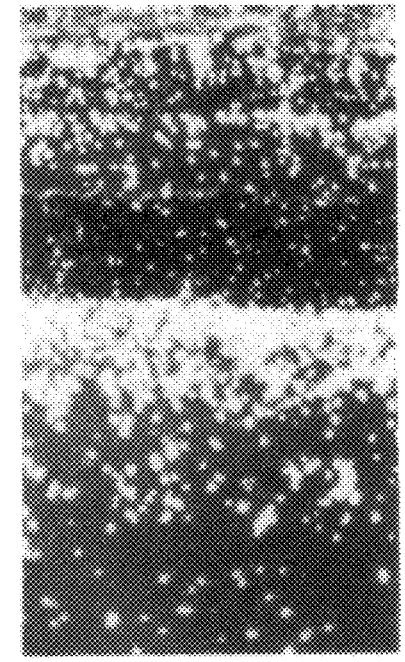

On a northern blot of rat retina, a 2.6 kB mRNA was also detected, and this mRNA was less abundant than that detected in striatum, but more abundant than that detected in cerebral cortex, hippocampus and brainstem (data not shown). As illustrated in FIGS. 1A and 1B, in situ hybridization histochemistry using sections of rat retina revealed hybridization to cells in the inner nuclear and in the outer plexiform layers. Hybridization was also detected in a few cells in the ganglion cell layer. No significant hybridization was detected in the outer nuclear layer, inner segments, outer segments, or the pigment epithelium (positive chemography of pigment epithelium with photographic emulsion makes detection of specific signal within those cells problematic). As illustrated in FIGS. 1C and 1D, a similar pattern of hybridization was detected in cryostat sections of monkey retina. Again, hybridization was detected in cells of the inner nuclear layer and outer plexiform layers, and no hybridization was detected in the other layers.

Molecular cloning of a homologous cDNA from human retina. Since the mixture of S1, S2 and S3 probes were able to detect a homologous mRNA which is present in primate retina, these probes were used to screen a human retinal lambda gt10 cDNA library lifted onto nylon filters. A duplicate set of lifts was screened with a mixture of the TM2 and TM3 probes. While the latter probes may not be expected to be selective for dopamine receptors, since the dopamine D2 receptor is homologous with all G-protein coupled receptors in the regions of these probes, they would be likely to detect the human homolog of the dopamine D2 receptor. Eight clones were positive with both sets of probes in the initial screens, and four of these hybridized with the n-terminal probe alone. Of these four, clone lambda 16A contained the largest cDNA insert (2.5 kB). This clone was subcloned into the Bluescript II Ks+ vector for sequence analysis and the pCD-PS vector for mammalian expression. An essentially pure culture of clone lambda 16A was deposited on Sep. 11, 1989 in the permanent collection of the American Type Culture Collection (ATCC), 12301 Parklawn Drive, Rockville, Md., U.S.A. 20852-1776 and assigned accession number ATCC 46654.

Comparison of the human and rat cDNAs. The nucleic acid sequence of clone 16A is shown in FIGS. 2A–2D. Comparison of the 5' untranslated sequences of the two cDNAs indicates a high degree of conservation, showing 91% identity. The short open reading frame located in the 5' region of the rat cDNA is conserved in the human cDNA. The coding regions of the two cDNAs are also highly conserved in sequence, showing 90% identity at the nucleic acid level. Comparison of the deduced amino acid sequences of the two proteins indicates the presence of 18 amino acid substitutions. Fourteen of these substitutions are conservative, and nine are located in the third cytoplasmic loop. The human receptor is one amino acid shorter, lacking an isoleucine in the third cytoplasmic loop. Four amino acid substitutions are present in the hydrophobic (hypothetically transmembrane) domains of the proteins. Two of these substitutions are conservative.

Mammalian expression of the human cDNA. Before transfection, COS-7 cells do not express binding sites for $^3$H-raclopride or $^3$H-SCH23396, which are displaced by chlorpromazine. After transfection with 16A-pCD-PS DNA, $^3$H-raclopride bound to COS-7 with high affinity $k_D$ 3.2 nM±0.4 and a maximum number of binding sites of 800±110 fmole/mg protein. $^3$H-SCH23396 did not show significant displacable binding to transfected COS-7 cells in concentrations up to 5 nM. Above these concentrations, significant binding was detected in transfected cells, but the $K_D$ and $B_{max}$ values could not be determined because of the very high levels of nonspecific binding observed at these ligand concentrations. As shown in FIG. 3, several dopaminergic drugs competed for the binding sites labeled by $^3$H-raclopride in transfected cells with high affinity. The rank order of potency was chlorpromazine>(−)

sulpiride>apomorphine>(+) sulpiride>dopamine. All of the ligands bound with mass action, not displaying Hill numbers which significantly differed from one.

Discussion

Within the inner retina there is good agreement between the distribution of dopamine D2 receptor mRNA and ligand binding. The regions with the highest concentrations of D2 ligand binding are the inner nuclear and outer plexiform layers. The mRNA distribution reported here directly parallels this distribution. One cell type located in the inner nuclear layer, which is physiologically known to have dopamine receptors, are dopaminergic amacrine cells, where D2 receptors inhibit the release of dopamine. Since D2 receptor mRNA is widely distributed throughout the inner nuclear layer, and dopaminergic cells are very rare, our data indicate that many other cell types must express this mRNA. We have not morphologically defined the phenotype of the few cells located in the ganglion cell layer that express high concentrations of D2 receptor mRNA. One possibility, which is consistent with their relative spareness, is that these cells represent displaced amacrine cells.

Within the outer retina, there is a marked difference in the distribution of D2 receptor mRNA and ligand binding. Binding data have indicated that a high concentration of dopamine D2 receptors are present in photoreceptors, being present in the outer nuclear layer, as well as inner and outer segments.

In addition to the binding data, physiological data collected from various species have indicated a physiological role for dopamine receptors on photoreceptor. Dearry and Burnside, *J. Neurochem.*, 44:1753–1763 (1985), incorporated herein by reference. In our experiments with both monkey and rat retina we have failed to detect mRNA within photoreceptors. The most likely explanation for this observation is that photoreceptors express dopamine D2 receptors which are encoded by a gene different from the one we examined.

Other evidence for a heterogeneity of dopamine D2 receptors was recently presented based on binding of $^3$H-spiperone to human retina. McGonigle et al., *Inv. Oph. & Visual Sci.*, 29:687–694 (1988), incorporated herein by reference. These data indicate that the substituted benzamide sulpiride discriminates among sites which have identical affinity for $^3$H-spiperone. The pharmacology of the receptor which we have cloned is like those which have the highest affinity for sulpiride. These data and the results of our experiments suggest that another D2 receptor subtype is yet to be cloned, which may be present in photoreceptors, and may have a lower affinity for substituted benzamides.

The human and rat dopamine D2 receptors are encoded by highly related genes. Since the encoded proteins have very few amino acid substitutions within their proposed transmembrane domains, one would predict that the two receptors would be highly related pharmacologically. This prediction is based on a hypothetical analogy to the beta adrenergic receptor. Beta receptors are structurally and functionally related to dopamine D2 receptors, and the transmembrane domains are largely responsible for its pharmacological properties. Dixon, op.cit. The predicted pharmological similarity between the rat and human receptors is born out by the expression data. The binding sites expressed in COS-7 cells by the human cDNA have many similarities to sites observed on expression of the rat gene, and sites observed in both human retina and rat brain. The fact that there are differences in the human and rat D2 receptors indicates the potential for subtle differences in their pharmacology. These data indicate the desirability of the use of human dopamine D2 receptors for drug development purposes.

The agonist pharmacologies of the cloned human and receptors do not agree with that observed for endogenously expressed receptors. For the receptors expressed by COS-7 cells, agonists show steep inhibition curves consistent with the presence of only a low affinity form of the receptor. One explanation for this phenomenon is that in COS-7 cells the very high levels of receptor saturate the endogenous G-proteins. In support for this possibility is the observation that when muscarinic receptors are expressed at similar levels in COS-7 cells, they show similarly steep inhibition curves (Brann et al., *FEBS Lett.*, 230:90–94 (1988), incorporated herein by reference), while these receptors are still able to functionally couple with G-proteins to stimulate inositol phosphate metabolism (J. Wess and N. R. Brann, unpublished observations). On the other hand, when these receptors are expressed at lower levels in A9 L cells, agonists show broad inhibition curves. Brann et al., *Mol. Pharm.*, 32:450–455 (1987), incorporated herein by reference.

In summary, we prepared a series of oligodeoxynucleotide probes, based on the sequence of a dopamine D2 receptor cloned from rat brain. A mixture of these probes hybridized with a 2.6 kB species of mRNA extracted from several rat tissues including retina, and using in situ hybridization of these probes to cryostat sections of rat retina, they densely labeled many cells in the inner nuclear and outerplexiform layers. A few cells were also labeled in the inner plexiform and ganglion cell layers. No hybridization was observed to the photoreceptor layers. A similar pattern of labeling was observed in monkey retina, indicating that the probes also hybridize with a homologous primate mRNA. The probes were used to screen a lambda gt10 library of human retina. A 2.5 kB clone was isolated which encodes a protein which differs from the rat brain protein by 18 amino acids. The 5' and 3' untranslated regions of the human retinal cDNA were also strongly the pCD-PS expression vector and transfected into COS-7 cells. The transfected cells bound $^3$H-raclopride with a pharmacology expected of dopamine D2 receptors. These data indicate that D2 receptors expressed by cells in the inner retina have genetic identity with those expressed by brain, and that the human and rat D2 receptors are derived from highly related genes.

EXAMPLE 2

Expression of a Human Dopamine D2 Receptor in A9 L Cells

In order to evaluate the pharmacological properties of the cloned D2 receptor with respect to agonists, it was necessary to express the receptor at levels which more closely approximate those found endogenously. It was also necessary to express the receptors in cells which express G-proteins and functional pathways which dopamine receptors normally activate.

A9 L cells were transformed using a modification of the calcium phosphate procedure. Chen and Okayama, *Mol. Cell. Biol.*, 7:2745–2752 (1987), incorporated herein by reference. On day one, cells were plated in six well plates and left to grow overnight. A twenty-fold excess of pCD-16A and pCD-neo were added to the cells in a calcium phosphate solution and left on the cells overnight. pCD-neo is a pCD mammalian expression vector which carries a gene that will confer resistance to neomycin. The cells were washed and subjected to selection with G418 for at least two weeks. Monoclonal cells lines were obtained at limiting dilution and selected based upon their ability to bind $^3$H-raclopride. Before transfection with pCD-16A and pCD-neo, A9 L cells do not specifically bind $^3$H-raclopride. After transfection and selection with G418, a monoclonal cell line was isolated that binds about 500 fmol/mg protein of $^3$H-raclopride. The cell line was designated A9 D2 Subclone 18. An essentially pure culture of cell line A9 D2 Subclone 18 was deposited on Sep. 13, 1989 in the permanent collection of the American Type Culture Collection (ATCC), 12301 Parklawn Drive, Rockville, Md., U.S.A. 20852-1776 and assigned accession number ATCC CRL 10225.

Cyclic AMP levels were measured as follows. Transfected A9 L cells from cell line A9 D2 Subclone 18 were incubated with dopamine for 10 minutes. The media was aspirated, and cells were lysed by the addition of 0.1 M HCl. Cyclic AMP was acetylated by the additional of acetic anyhydride. Acetyl-cAMP levels were measured using an automated radioimmunoassay (Gammaflow, Ato instruments) with $^{125}$I-cAMP (G. Brooker, Georgetown University) as a tracer and an antibody to acetyl-cAMP. The dopamine decreased cAMP levels with an $ED_{50}$ of 40 nM in these transfected cells. See FIG. 4. Thus, the receptor was stably expressed in A9 L cells, were dopamine was able to decrease cAMP levels.

It will be apparent to those skilled in the art that various modifications and variations can be made to the products and processes of the present invention. Thus, it is intended that the present invention cover such modifications and variations, provided they come within the scope of the appended claims and their equivalents.

We claim:

1. An isolated or essentially pure cDNA molecule whose nucleotide sequence encodes a human dopamine D2 receptor, wherein said receptor is a polypeptide having the amino acid sequence shown in FIGS. 2A–2D.

2. The cDNA molecule of claim 1 whose nucleotide sequence encodes a human dopamine D2 receptor, wherein said sequence comprises the nucleotide sequence 0–1241 shown in FIGS. 2A–2D.

3. A recombinant DNA comprising the cDNA molecule of claim 2 operably linked to control nucleotide sequences capable of expressing said cDNA in a compatible host.

4. An isolated pure clone from a human tissue DNA library, wherein said clone contains an isolated or essentially pure cDNA molecule whose sequence encodes a human dopamine D2 receptor, wherein said sequence comprises the nucleotide sequence 0–1241 shown in FIGS. 2A–2D.

5. Clone lambda 16A assigned accession number ATCC 40654 by the American Type Culture Collection.

6. A vector for expressing the human dopamine D2 receptor whose amino acid sequence is given in FIGS. 2A–2D in a compatible host, said vector comprising an expression vector capable of transforming a procaryotic or eucaryotic cell and the cDNA described in claim 2 inserted into said vector in proper orientation and correct reading frame for expression of the human dopamine D2 receptor encoded therein.

7. A DNA molecule comprising a sequence which is fully complementary to the nucleotide sequence of the cDNA molecule whose sequence encodes a human dopamine D2 receptor, wherein said cDNA sequence comprises the nucleotide sequence 0–1241 shown in FIGS. 2A–2D.

8. A cell transformed with the vector described in claim 6.

9. A mammalian cell line comprising a mammalian cell stably transfected with the vector described in claim 6 and capable of continuous growth in a suitable culture medium.

10. The mammalian cell line described in claim 9 wherein said mammalian cell is selected from the group consisting of a neuronal cell, a fibroblast cell, an epithelial cell, and a glial cell.

11. The mammalian cell line described in claim 9 wherein the cells of said cell line express the human D2 dopamine receptor whose amino acid sequence is given in FIGS. 2A–2D.

* * * * *